United States Patent [19]

Pusateri et al.

[11] Patent Number: 5,686,108
[45] Date of Patent: Nov. 11, 1997

[54] BRASSICA VEGETABLE SUPPLEMENT AND PROCESS FOR MANUFACTURE

[75] Inventors: Donald J. Pusateri, Hemet; William C. Chiang, Irvine; Richard E. A. Letiz, Hemet; Phelicia M. Sperrazzo, Redlands, all of Calif.

[73] Assignee: Amway Corporation, Ada, Mich.

[21] Appl. No.: 534,645

[22] Filed: Sep. 27, 1995

[51] Int. Cl.$^6$ .............................. A61K 9/20; A61K 9/14
[52] U.S. Cl. ............................................ 424/464; 424/489
[58] Field of Search .................................. 424/464, 489, 424/451

[56] References Cited

U.S. PATENT DOCUMENTS

| | | | |
|---|---|---|---|
| 98,875 | 1/1870 | Mays et al. | 424/195.1 |
| 4,083,836 | 4/1978 | Anjou et al. | 426/417 |
| 4,244,973 | 1/1981 | van Megen | 426/49 |
| 4,338,350 | 7/1982 | Chen et al. | 426/658 |
| 4,496,598 | 1/1985 | Sakai et al. | 426/417 |
| 5,248,504 | 9/1993 | Friedman | 424/434 |
| 5,411,986 | 5/1995 | Cho et al. | 514/514 |

OTHER PUBLICATIONS

Glucosinolates and Derived Products in Cruciferous Vegetables. Identification of Organic Nitriles from Cabbage, *J. Agric. Food Chem.*, vol. 25, No. 1, 1977.

Glucosinolate Products in Commercial Sauerkraut, *J. Agric. Food Chem.*, 1980, 28, 809–811.

Production of Toxic Glucosinolate Derivatives from Rapeseed Meal by Intestinal Microflora of Rat and Chicken, *J. Sci. Food Agric*, 1988, 43, 299–308.

Effects of 1–Isothiocyanato–3–(Methylsulfinyl)–Propane on Xenobiotic Metabolizing Enzymes in Rats, *Fd. Chem. Toxic.*, vol. 31, No. 10, pp. 723–729, 1993.

Effect of Organic Reducing Agents and Ferrous Ion on Thioglucosidase Activity of Crambe Abyssinica Seed, *Canadian Journal of Biochemistry*, vol. 48, 1970.

Rapid Detection of Inducers of Enzymes that Protect Against Carcinogens, *Proc. Natl. Acad. Sci.* USA 89 (1992).

Influence of Some Management Parameters on Glucosinolate Levels in Brassica Forage, *Agronomy Journal*, vol. 77, Jul.–Aug. 1985.

Distribution and Metabolism of the Natural Anticarcinogen Phenethyl Isothiocynate in A/J Mice, *Carcinogenesis*, vol. 11, No. 11, pp. 2033–2036, 1990.

Anticarcinogenic Activities of Sulforaphane and Structurally Related Synthetic Norbornyl Isothiocyanates, *Proc. Natl. Acad. Sci.*, USA 91, (1994).

1–Cyano–3, 4–Epithiobutane: A Major Product of Glucosinolate Hydrolysis in Seeds From Certain Varieties of Brassica Campestris, *Phytochemistry*, 1974, col. 13, pp. 2611–2615.

Nutrients and Toxicants in Rapeseed Meal: A Review, *Journal of Animal Science*, vol. 58, No. 4, 1984.

Myrosinase Activity of Cruciferous Vegetables, *Sci. Food Agric.*, 1984, 35, 543–552.

Detoxification of Commercial United Kingdom Rapeseed Meal by Glucosinolate Hydrolysis with Exogenous Myrosinase and the Extractability of the Aglucones by Aqueous Industrial Methylated Spirits, *J. Sci. Food Agric.*, 1989, 46, 331–337.

A Major Inducer of Anticarcinogenic Protective Enzymes From Broccoli: Isolation and Elucidation of Structure, *Proc. Natl. Acad. Sci.*, USA, 89 (1992).

Methods for Glucosinolate Analysis, *Methods in Plant Biochemistry*, vol. 8, ISBN 0–12–461018–8, 1993.

Aspects on the Use of Headspace GC On–Column Injections in Flavor Research, *Journal of Chromatographic Science*, vol. 26, Nov. 1988.

High–Performance Liquid Chromatographic Analysis of Anticarcinogenic Indoles in Brassica Oleracea, *J. Agric. Food Chem.* 1987, 35, 46–49.

Separation of Desulphoglucosinolates by Reversed–Phase High–Performance Liquid Chromatography, *Journal of Chromatography*, 247 (1982), 141–148.

Study on Volatile Isothiocyanate Detected in Cultivar of Brassica Vegetable (Part 2) Analysis of Flavour of Cabbage by Gas–Chromatography–Mass Spectrometry, (Rept. Natl. Food Res. Inst.) No. 47, 41–48 (1985).

HPLC Separation of Glucosinolates from Leaves and Seeds of Arabidopis Thaliana and Their Identification Using Thermospray Liquid Chromatography/Mass Spectrometry, *Journal of Chromatographic Science*, vol. 26, Nov. 1988.

Purification of the w–(Methylsulfinyl)alkyl Glucosinolate Hydrolysis Products: 1–Isothiocyanato–3–(Methylsulfinyl)Propane, 1–Isothiocyanato–4–(Methylsulfinyl)Butane, 4–(Methylsulfinyl)Butanenitrile, and 5–(Methylsulfinyl)Pentanenitrile from Broccoli and Lesquerella Fendleri, *J. Agric. Food Chem.*, 1993, 41, 89–95.

Glucosinolates in Rapeseeds: Analytical Aspects, Proceedings of a Seminar in the CEC Programme of Research on Plant Producitivity, held in Gembloux (Belgium), 1–3 Oct. 1986.

GCIRC Eighth International Rapeseed Congress, vol. 5 of 6, Jul. 1991.

Formation of Organic Nitriles from Progoitrins in Leaves of Crambe Abyssinica and Brassica Napus, *J. Agr. Food Chem.*, vol. 19, No. 1, 1971.

Goitrogenic Activity of Allylisothiocyanate—A Widespread Natural Mustard Oil, vol. 76, Jan. 1965.

(List continued on next page.)

*Primary Examiner*—Thurman K. Page
*Assistant Examiner*—James M. Spear

[57] ABSTRACT

A brassica vegetable tablet contains at least 50 ug of sulforaphane and a maximum of 50 ug of sulforaphanenitrile. A process for producing a brassica vegetable product includes inactivating endogenous myrosinase enzyme in a brassica vegetable and thereafter blending the vegetable with exogenous myrosinase enzyme. The preferred process may include steam blanching as the method of inactivating the endogenous myrosinase enzyme. The preferred process may also include horseradish root as the source of exogenous myrosinase enzyme.

29 Claims, No Drawings

OTHER PUBLICATIONS

Glucosinolates and Derived Products in Cruciferous Vegetables. Identification of Organic Nitriles from Cabbage, *J. Agric. Food Chem.*, vol. 25, No. 1, 1977.

Effect of Organic Reducing Agents and Ferrous Ion on Thioglucosidase Activity of Crambe Abyssinica Seed, *Canadian Journal of Biochemistry*, vol. 48, 1970.

Isolation and Identification of Trans-4-(Methylthio)-3-Butenyl Glucosinolate from Radish Roots (Raphanus Sativus L.), *J. Agric. Food Chem.*, 1992, 40, 1687–1691.

In Vitro Activity of Some Glucosinolates and Their Reaction Products Toward a Population of the Nematode Heterodera Schachtii, *J. Agric. Food Chem.*, 1993, 41, 825–829.

Glucosinolates and Derived Products in Cruciferous Vegetables. Analysis of the Edible Part from Twenty-Two Varieties of Cabbage, *J. Agric. Food Chem.*, vol. 24, No. 3, 1976.

Glucosinolate Products in Commercial Sauerkraut, *J. Agric. Food Chem.*, 1980, 28, 809–811.

Identification and Quantification of Organosulfur Compliance Mark in a Garlic Extract, *J. Agric. Food Chem.*, 1993, 41, 37–41.

*Journal of Agricultural Research*, vol. 67, Jul. 1–Dec. 15, 1943.

Volatile Isothiocyanates and Nitriles from Glucosinolates in Rutabaga and Turnip, *J. Amer. Soc. Hort. Sci.* 107(6):1050–1054, 1982.

High-Performance Liquid Chromatography and Gas Chromatography of Organic Isothiocyanates and their Methanol-Isothiocyanate Addition Compounds, *Journal of Chromatography*, 155 (1978) 198–202.

Dimeric Structure of a Sulfoxide, *Journal of the American Chemical Society*, 87:3, Feb. 5, 1965.

Isothiocyanates XIV, 5-Methylthiopentyl Isothiocyanate, a New Mustard Oil Present in Nature as a Glucoside (Glucoberteroin), *Acta Chem. Scand.* 9 (1955) No. 8.

Collection of Czechoslovak Chemical Communications, 5, XXIV, 1959.

Isothiocyanates XXX. Glucohirsutin, a New Naturally Occurring Glucoside Furnishing (–)-8-Methylsulphinyl-1-Octyl Isothiocyanate on Enzymic Hydrolysis, *Acta Chem. Scand.* 12 (1958) No. 5.

Isothiocyanates VIII, Synthesis of p-Hydroxybenzyl Isothiocyanate and Demonstration of its Presence in the Glucoside of White Mustard (Sinapis alba L.), *Acta Chem. Scand.* 8 (1954) No. 4.

Absorption Spectra of Alkyl Isothiocyanates and N-Alkyl Monothiocarbamates, *Acta Chem. Scand.* 13 (1959) No. 3.

Progress in the Chemistry of Organic Natural Products, 1960.

1994 IFT Annual Meeting/Book of Abstracts, p. 217, 72–6.

Beyond Vitamins, *Newsweek, Apr. 25, 1994, pp. 45–49*.

Elevation of Serum Phase II Enzymes by Anticarcinogenic Enzyme Inducers: Makers for a Chemoprotected State? pp. 2441–2445, 1993.

Cancer Chemoprevention by Phytochemicals in Fruits and Vegetables, Chapter 1, 1994.

The Biology and Chemistry of the Cruciferae, *Academic Press*, 1976, pp. 191–205.

Cancer Preventive Properties of Varieties of Brassica Oleracea: A Review, *Am. J. Clin. Nutr.*, 1994, pp. 1166–1170.

BRASSICA VEGETABLE SUPPLEMENT AND PROCESS FOR MANUFACTURE

BACKGROUND OF THE INVENTION

The present invention relates to a brassica vegetable concentrate and supplement containing high levels of sulforaphane and minimal levels of sulforaphane-nitrile and the method of making it.

Although consumers are increasingly more aware of the relationship of brassica vegetables to health and disease, many people don't reap these benefits because they don't like the taste of the vegetables or they find them cumbersome to eat. Broccoli, as well as other brassica vegetables, may be helpful in fighting disease because they contain glucosinolates. Glucosinolates are converted to isothiocyanates, such as sulforaphane, by myrosinase enzymes, a group of enzymes that are naturally present in brassica vegetables. Sulforaphane and other isothiocyanates help the body to fight disease by inducing a group of enzymes capable of detoxifying carcinogens in the body.

Unfortunately for consumers, myrosinase enzymes contact the glucosinolate when the cells of the brassica vegetable are disrupted such as by chewing or milling. Therefore, those consumers who don't like the taste of broccoli, yet don't want to pass up its health benefits, must force themselves to eat something they don't like. In addition, glucosinolates can also be converted by myrosinase enzymes into nitriles such as sulforaphane-nitrile, non-nutrients that are contraindicated for health. Therefore, there is a need for a brassica supplement that has high levels of sulforaphane but low levels of sulforaphane-nitrile.

At the present time, a suitable brassica vegetable supplement or concentrate is not available. Typically, prior art brassica tablets, such as broccoli tablets, are made by dehydrating the fresh vegetable, grinding the vegetable into a powder form and thereafter forming a tablet or supplement. High temperature dehydration, however, inactivates the endogenous (naturally present) myrosinase enzymes. Consequently, it is hypothesized that when the supplement is ingested, the conversion of the glucosinolates to isothiocyanates cannot occur via the aforementioned plant pathway. It has also been suggested to make brassica tablets by freeze-drying the vegetable. In this method, the endogenous myrosinase enzymes are not inactivated in the final product. However, the enzymes contained in the tablet are not active at the low pH of stomach acids (when the supplement is swallowed before it can convert the glucosinolates into isothiocyanates).

A process that produces a brassica vegetable supplement or concentrate with high levels of sulforaphane and minimal sulforaphane-nitrile is desired. Such a process should maximize the conversion of the parent glucosinolates (gluocoraphanin) to sulforaphane while minimizing the presence of sulforaphane-nitrile. Therefore, the resulting supplement or concentrate must contain preformed sulforaphane in lieu of the parent glucosinolate and corresponding myrosinase enzymes where conversion is subject to environmental conditions.

SUMMARY OF THE INVENTION

The present invention includes a brassica vegetable supplement or concentrate and a method of making it. The brassica vegetable supplement of the present invention comprises at least 50 ug of sulforaphane and a maximum of 50 ug of sulforaphane-nitrile. More preferably, the tablet comprises at least 100 ug of sulforaphane and no more than 20 ug of sulforaphane-nitrile. In the most preferred embodiment, the tablet includes 1,000 ug of sulforaphane and a maximum of 10 ug sulforaphane-nitrile.

The process for producing the brassica vegetable supplement of the present invention includes inactivating the endogenous myrosinase enzymes in brassica vegetables and thereafter blending the vegetables with exogenous sources of myrosinase enzymes. More specifically, the process of the present invention includes harvesting broccoli to minimize broccoli stem material, blanching fresh broccoli to inactivate endogenous myrosinase enzymes, blending the steamed broccoli with a source of exogenous myrosinase enzymes, preparing a homogenate from the blended broccoli and exogenous myrosinase enzymes, centrifuging the homogenate, concentrating the supernatant by low heat vacuum concentration, adding a carrier such as starch, maltodextrin, sucrose, dextrose anti vegetable gums to the concentrated supernatant, lowering the pH to 3.5, forming a powder by drying the concentrate and carrier, and forming a tablet from the powder.

One of the advantages of the process of the present invention is that it maximizes the conversion of glucoraphanin (a specific glucosinolate) to sulforaphane while minimizing the presence of sulforaphane-nitrile.

DETAILED DESCRIPTION AND PREFERRED EMBODIMENTS OF THE INVENTION

The present invention includes a brassica vegetable supplement with high levels of sulforaphane and low levels of sulforaphane-nitrile. The process for making the product comprises inactivating endogenous myrosinase enzymes in brassica vegetables and blending the vegetables with active exogenous myrosinase enzymes.

In particular, the brassica vegetable product is a supplement product which can take any form such as liquid, powder, tablet or capsule containing sulforaphane levels of 50 ug with no more than 50 ug sulforaphane-nitrile. More preferably, the tablet contains 100 ug of sulforaphane and a maximum of 20 ug of sulforaphane-nitrile. Most preferably, the tablet contains 1,000 ug of sulforaphane and a maximum of 10 ug of sulforaphane-nitrile.

The preparations and products of the present invention may vary widely in composition. The process requires brassica vegetables. Brassica vegetables include, but are not limited to, cabbage, kale, cauliflower, broccoli, mustard greens, kohlrabi, Brussels sprouts, turnips and horseradish root. The most desirable brassica vegetable for this process is broccoli. Although the entire broccoli plant may be used, the broccoli floret is preferred as it has been found that the stem material contains more nitrile than the floret. In the following discussion, the process for making the supplement of the present invention will be described with reference to broccoli. It is to be understood however, that the use of the other brassica vegetables is contemplated.

The broccoli must be treated so that its endogenous myrosinase enzymes are inactivated. Inactivation may occur by any method presently known in the art including, but not limited to, steaming, blanching and immersing in ethanol. In the preferred method, the broccoli is steam blanched. Steam blanching preferably occurs at a temperature in the range of 80°–100° C., more preferably in the range of 90°–100° C, and most preferably at 100° C. The duration of steam blanching also affects the deactivation of the myrosinase enzymes. Steam blanching therefore proceeds for at least 0.5–15 min., more preferably 2.0–8 min., and most preferably 3–5 min.

After the broccoli has been steamed at the requisite temperature and for a duration sufficient to inactivate the myrosinase enzymes, exogenous myrosinase enzyme and water are added. The exogenous myrosinase enzyme may be taken from any source, natural or commercial. An example of a commercial variety of myrosinase enzyme is thioglucosidase from Sigma Chemical Co., St. Louis, Mo., EC 3.2.3.1. Preferably, the exogenous myrosinase enzyme is taken from a natural source, more preferably form a brassica vegetable such as, but not limited to, broccoli, kale, Brussels sprouts, turnips, cabbage leaves, cauliflower, mustard greens, kohlrabi, and horseradish root. The most preferable source of exogenous myrosinase enzyme for this process is fresh horseradish root. Preferably, fresh horseradish is added to fresh, blanched broccoli in the range of 3–10%, and more preferably is added in the range of 3–8%. Most preferably, fresh horseradish is added to broccoli in the range of 4–6%, with optimum being 5%. The blanched vegetables, exogenous myrosinase enzyme and water are then milled. Milling may occur by any method known in the art. Preferably, an Urshell Mill is used (with a 0.030" screen) to pre-mill the material with the added water. The pre-milled material is then put through a colloid mill to form a very fine slurry. The slurry is then mixed in a tank for approximately 0.5–3 hours, more preferably 1–2 hours, and most preferably 2 hours.

After the exogenous myrosinase enzymes, water and blanched vegetables are sufficiently mixed, the mixture is centrifuged, the supernatant concentrated, the pH is adjusted, and, thereafter, processed to form a powder. This may be accomplished by any method known in the art. Preferably, the concentrate is mixed with a carrier. Any carrier will work, and preferably a carrier selected from the group consisting of sucrose, dextrose, starch and vegetable gums can be used. The mixture is then dried through any conventional method such as freeze drying, or spray drying, with spray drying being the preferred method. Alternatively, prior to drying, the pH of the concentrate is adjusted to 3.5. The powder may be further processed into any form appropriate for consumer use, such as powdered food and beverage supplements, tablets and capsules. Preferably, a broccoli tablet is formed.

The process of the present invention is an improvement over the prior art because it maximizes the conversion of glucoraphanin to sulforaphane while minimizing the presence of sulforaphane-nitrile. Specifically, the process inhibits the conversion of glucoraphanin to sulforaphane-nitrile by inactivating the endogenous myrosinase enzyme. The glucoraphanin is then converted to sulforaphane by the addition of exogenous myrosinase enzymes.

Although the present invention has been disclosed with respect to a preferred embodiment, further modifications will be apparent to those skilled in the art. Accordingly, it is not intended that the invention be limited by the disclosure or by such modifications, but instead that its scope should be determined entirely by reference to the claims which follow herein below.

What is claimed:

1. A process for producing a brassica vegetable product with high levels of sulforaphane and low levels of sulforaphane-nitrile comprising the steps of:
   (a) deactivating endogenous myrosinase enzyme in a brassica vegetable; and
   (b) blending the vegetable with exogenous myrosinase enzyme, wherein the product contains at least about 50 μg of sulforaphane and a maximum of about 50 μg sulforaphane-nitrile.

2. The process for producing the brassica vegetable product of claim 1 wherein the endogenous myrosinase enzyme is inactivated by steam blanching.

3. The process for producing a brassica vegetable product of claim 1 wherein the brassica vegetable is selected from the group consisting of cabbage, Brussels sprouts, kale, cauliflower, turnip, broccoli, mustard greens, kohlrabi, and horseradish root.

4. The process for producing the brassica vegetable product of claim 1 wherein the brassica vegetable is broccoli.

5. The process for producing the brassica vegetable product of claim 1 wherein the source of exogenous enzyme is a brassica vegetable or mixture thereof.

6. A process for producing a brassica vegetable product with high levels of sulforaphane and low levels of sulforaphane-nitrile comprising the steps of:
   (a) deactivating endogenous myrosinase enzyme in a brassica vegetable; and
   (b) blending the vegetable with exogenous myrosinase enzyme.

7. The process for producing the brassica product of claim 6 wherein the endogenous myrosinase enzyme is inactivated by steam blanching.

8. The process for producing the brassica vegetable product of claim 6 wherein the brassica vegetable is selected from the group consisting of cabbage, Brussels sprouts, kale, cauliflower, turnip, broccoli, mustard greens, kohlrabi and horseradish root.

9. The process for producing the brassica vegetable product of claim 6 wherein the brassica vegetable is broccoli.

10. The process for producing the brassica vegetable product of claim 6 wherein the source of the exogenous enzyme is a brassica vegetable or mixtures thereof.

11. The process for producing the brassica vegetable product of claim 6 wherein the source of the exogenous enzyme is horseradish root.

12. The process of claim 6 wherein the brassica vegetable product contains at least about 50 ug sulforaphane and a maximum of about 50 ug sulforaphane-nitrile.

13. The process for producing the brassica product of claim 6 further comprising the steps of:
   (a) preparing a slurry from the blended vegetable and exogenous enzyme;
   (b) passing the slurry through a centrifuge;
   (c) preparing a powder from the supernatant; and
   (d) forming the powder into a tablet.

14. A process for producing a broccoli tablet with high levels of sulforaphane and low levels of sulforaphane-nitrile comprising the steps of:
   (a) steaming fresh broccoli to inactivate endogenous myrosinase enzyme;
   (b) blending the blanched broccoli with a source of exogenous myrosinase enzyme;
   (c) preparing a slurry from the blended broccoli and exogenous myrosinase enzyme;
   (d) passing the slurry through a centrifuge;
   (e) forming a powder from the supernatant; and
   (f) forming a broccoli tablet from the powder, wherein the tablet contains at least about 50 ug sulforaphane and a maximum of about 50 ug sulforaphane-nitrile.

15. The process recited in claim 14 wherein the steaming is performed at a temperature of about 100° C.

16. The process of claim 14 wherein the source of exogenous myrosinase enzyme is horseradish root.

17. A process for preparing a broccoli tablet with high levels of sulforaphane and low levels of sulforaphane-nitrile comprising the steps of:

(a) inhibiting conversion of glucoraphanin in fresh broccoli to sulforaphane-nitrile by inactivating myrosinase enzymes in the broccoli;

(b) converting glucoraphanin in fresh broccoli to sulforaphane by adding exogenous myrosinase enzymes; and (c) preparing a tablet.

18. A brassica vegetable tablet comprising at least about 50 ug by weight of sulforaphane and a maximum of about 50 ug by weight of sulforaphane-nitrile prepared by a process comprising the steps of:

(a) inactivating endogenous myrosinase enzyme in a brassica vegetable; and (b) blending the vegetable with exogenous myrosinase enzyme.

19. The brassica vegetable tablet prepared by the process of claim 18 wherein the endogenous myrosinase enzyme is inactivated by steam blanching.

20. The brassica vegetable tablet prepared by the process of claim 18 wherein the endogenous myrosinase enzyme is inactivated by immersing the brassica vegetable in ethanol.

21. The brassica vegetable tablet prepared by the process of claim 18 wherein the endogenous myrosinase enzyme is inactivated by water blanching.

22. The brassica vegetable tablet prepared by the process of claim 18 wherein the brassica vegetable is selected from the group consisting of cabbage, Brussels sprouts, kale, cauliflower, turnip, broccoli, mustard greens, kohlrabi and horseradish root.

23. The brassica vegetable tablet prepared by the process of claim 18 wherein the brassica vegetable is broccoli.

24. The brassica vegetable tablet prepared by the process of claim 18 wherein the source of the exogenous enzyme is a brassica vegetable or mixtures thereof.

25. The brassica vegetable tablet prepared by the process of claim 18 wherein the source of the exogenous enzyme is horseradish root.

26. The brassica vegetable tablet prepared by the process of claim 18 comprising the steps of:

(a) preparing a slurry from the blended vegetable and exogenous enzyme;

(b) passing the slurry through a centrifuge;

(c) preparing a powder from the supernatant; and (d) forming the powder into a tablet.

27. The process for producing the brassica vegetable product of claim 1 wherein the source of exogenous enzyme is horseradish root.

28. The process for producing the brassica vegetable product of claim 1 further comprising the steps of:

(a) preparing a slurry from the blended vegetable and exogenous enzyme;

(b) passing the slurry through a centrifuge;

(c) preparing a powder from the supernatant; and (d) forming the powder into a tablet.

29. A process for preparing a broccoli tablet with high levels of sulforaphane and low levels of sulforaphane-nitrile comprising the steps of:

(a) inhibiting conversion of glucoraphanin in fresh broccoli to sulforaphane-nitrile by inactivating myrosinase enzymes in the broccoli;

(b) converting glucoraphanin in fresh broccoli to sulforaphane by adding exogenous myrosinase enzymes; and (c) preparing a tablet, wherein said tablet contains at least about 50 ug sulforaphane and a maximum of about 50 ug of sulforaphane-nitrile.

* * * * *